United States Patent
Kimura et al.

(10) Patent No.: US 11,578,349 B2
(45) Date of Patent: Feb. 14, 2023

(54) MULTISTEP MANUFACTURING METHOD FOR PRODUCING FERMENTATION PRODUCT, WHICH INCLUDES CULTURING MICROORGANISM

(71) Applicant: KAO CORPORATION, Tokyo (JP)

(72) Inventors: Shunsuke Kimura, Kamisu (JP); Kenichi Shikata, Kamisu (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/969,812

(22) PCT Filed: Feb. 13, 2019

(86) PCT No.: PCT/JP2019/005172
§ 371 (c)(1),
(2) Date: Aug. 13, 2020

(87) PCT Pub. No.: WO2019/159991
PCT Pub. Date: Aug. 22, 2019

(65) Prior Publication Data
US 2020/0377923 A1 Dec. 3, 2020

(30) Foreign Application Priority Data
Feb. 13, 2018 (JP) .............................. JP2018-022774

(51) Int. Cl.
| | | |
|---|---|---|
| C12P 21/04 | (2006.01) | |
| C12P 21/02 | (2006.01) | |
| B01D 15/10 | (2006.01) | |
| C12N 9/54 | (2006.01) | |

(52) U.S. Cl.
CPC .............. *C12P 21/02* (2013.01); *B01D 15/10* (2013.01); *C12N 9/54* (2013.01)

(58) Field of Classification Search
CPC ...................................................... C12P 21/02
See application file for complete search history.

(56) References Cited

U.S. PATENT DOCUMENTS

| | | |
|---|---|---|
| 4,029,548 A | 6/1977 | Argoudelis et al. |
| 2018/0230500 A1 | 8/2018 | Chauve et al. |

FOREIGN PATENT DOCUMENTS

| | | | | |
|---|---|---|---|---|
| JP | 3-240487 A | 10/1991 | | |
| JP | 2011-36146 A | 2/2011 | | |
| JP | 2016-96742 A | 5/2016 | | |
| JP | 2017-112847 A | 6/2017 | | |
| WO | WO-2010086840 A2 * | 8/2010 | ................ | C12P 7/06 |
| WO | WO 2010/110448 A1 | 9/2010 | | |
| WO | WO 2017/025339 A1 | 2/2017 | | |

OTHER PUBLICATIONS

Wang et al, Improved propionic acid and 5,6-dimethylbenzimidazole control strategy for vitamin B12 fermentation by Propionibacterium freudenreichii. Journal of Biotechnology vol. 193, Jan. 10, 2015, pp. 123-129.*
Hansson et al, Single-Step Recovery of a Secreted Recombinant Protein by Expanded Bed Adsorption. Bio/Technology vol. 12, pp. 285-288 (1994).*
Takami et al, Production of extremely thermostable alkaline protease from *Bacillas* sp. No. AH-101 Appl Microbiol Biotechnol (1989) 30:120-12.*
Saffarionpoura et al, Selective adsorption of flavor-active components on hydrophobic resins. Journal of Chromatography A, 1476 (2016) 25-34 .*
Mitsubishi Chemical Corp, Inc Sepabeads SP2MGS, DIAON (2013).*
Pharmacia Biotech Inc, Streamline DEAE (1995).*
Erickson, Size and Shape of Protein Molecules at the Nanometer Level Determined by Sedimentation, Gel Filtration, and Electron Microscopy. Biological Procedures Online, vol. 11, No. 1 ,May 15, 2009;11:32-51.*
Sherman, F. "Getting Started with Yeast". Methods Enzymology. 2002. vol. 350. p. 3-41.*
International Search Report, issued in PCT/JP2019/005172, PCT/ISA/210, dated May 14, 2019.
Extended European Search Report for European Application No. 19754243.4, dated Nov. 9, 2021.
Stanbury et al., "The recovery and purification of fermentation products," Principles of Fermentation Technology, 2017, pp. 619-686, 68 pages total.

* cited by examiner

*Primary Examiner* — Yong D Pak
(74) *Attorney, Agent, or Firm* — Birch, Stewart, Kolasch & Birch, LLP

(57) ABSTRACT

A method for manufacturing a fermentation product by culturing a microorganism, the method containing steps (A) to (D):
 (A) culturing the microorganism with a first culture medium;
 (B) passing a culture solution containing cultured bacterial cells, raw materials for culture, and the fermentation product through an adsorption tower packed with an adsorbent capable of adsorbing the fermentation product from the culture solution, and then collecting an effluent containing the bacterial cells and the raw materials for culture flowing out from the adsorption tower, wherein a relationship among a size (short diameter) d of the bacterial cell, a pore size D1 of the adsorbent, and a minimum void size D2 between adsorbent particles, $D1 < d < D2$ is satisfied;
 (C) eluting the fermentation product from the absorbent; and
 (D) culturing the microorganism with a second culture medium using collected effluent containing the bacterial cells and the raw materials for culture.

20 Claims, No Drawings
Specification includes a Sequence Listing.

_US 11,578,349 B2_

SEQUENCE LISTING

<160> NUMBER OF SEQ ID NOS: 7

<210> SEQ ID NO 1
<211> LENGTH: 434
<212> TYPE: PRT
<213> ORGANISM: Bacillus sp.

```
<400> SEQUENCE: 1

Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Thr Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
    290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
        355                 360                 365

Asp Leu Val Ile Thr Ala Pro Asn Gly Thr Gln Tyr Val Gly Asn Asp
    370                 375                 380

Phe Thr Ser Pro Tyr Asn Asp Asn Trp Asp Gly Arg Asn Asn Val Glu
385                 390                 395                 400
```

-continued

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
        420                 425                 430

Val Asn

<210> SEQ ID NO 2
<211> LENGTH: 45
<212> TYPE: DNA
<213> ORGANISM: Artificial Sequence
<220> FEATURE:
<223> OTHER INFORMATION: trpB-F

<400> SEQUENCE: 2
gaatgaaata ggcagatacg gtgattttgg cggaaagttt gttcc          45

<210> SEQ ID NO 3
<211> LENGTH: 45
<212> TYPE: DNA
<213> ORGANISM: Artificial Sequence
<220> FEATURE:
<223> OTHER INFORMATION: PrrnO-catsd-R

<400> SEQUENCE: 3
ttgatatgcc tcctaaattt ttatctaaag tgtctcaaag cgact          45

<210> SEQ ID NO 4
<211> LENGTH: 45
<212> TYPE: DNA
<213> ORGANISM: Artificial Sequence
<220> FEATURE:
<223> OTHER INFORMATION: PrrnO-cat-erm-F

<400> SEQUENCE: 4
tatgaggatg aagaagcggt ggatgcgtgt tcgtgctgac ttgca          45

<210> SEQ ID NO 5
<211> LENGTH: 45
<212> TYPE: DNA
<213> ORGANISM: Artificial Sequence
<220> FEATURE:
<223> OTHER INFORMATION: hisC-R2

<400> SEQUENCE: 5
ataaaatgca ttttcaaaca ggaactcctt cgcagcggcc actcc          45

<210> SEQ ID NO 6
<211> LENGTH: 45
<212> TYPE: DNA
<213> ORGANISM: Artificial Sequence
<220> FEATURE:
<223> OTHER INFORMATION: PrrnO-P-F

<400> SEQUENCE: 6
aaaaatttag gaggcatatc aaatgagaag aagaaaaag gtctt          45

<210> SEQ ID NO 7
<211> LENGTH: 45
<212> TYPE: DNA
<213> ORGANISM: Artificial Sequence
<220> FEATURE:
<223> OTHER INFORMATION: PrrnO-P-R

```
<400> SEQUENCE: 7
ccaccgcttc ttcatcctca tattaattca caattgccaa cgaga          45
```

MULTISTEP MANUFACTURING METHOD FOR PRODUCING FERMENTATION PRODUCT, WHICH INCLUDES CULTURING MICROORGANISM

FIELD OF THE INVENTION

The present invention relates to a method for the production of fermentation products using microorganisms.

BACKGROUND OF THE INVENTION

In recent years, technologies for producing industrially useful compounds by fermentation methods using microorganisms have been put into practical use.

In the fermentation culture solution after culturing of microorganisms, unused raw materials for culture and bacterial cells are contaminated with fermentation products. Therefore, it is common to first separate the bacterial cells and then separate the fermentation products from the solution containing the unused culture raw materials to recover them in the procedure for obtaining fermentation products from the culture solution. For the separation, centrifugal separation, membrane separation, adsorptive separation, and the like (e.g., Patent Literatures 1 to 3) are employed.

It has also been reported that a culture solution is filtered through a porous ceramic membrane to separate bacterial cells and at the same time to have enzymes contained in the culture solution specifically adsorbed on the membrane, and after the filtered cultured solution is removed, the enzyme is recovered by eluting (Patent Literature 4).

However, in these conventional methods, the bacteria may be reused, but the unused raw materials for culture are often discarded in the procedure of recovering the fermentation product and were seldom reused in the production of the fermentation product. Because a eutrophic liquid medium is often used as the medium for fermentation production, it is desired to use the raw material for culture effectively from an economic point of view.

(Patent Literature 1) JP-A-2016-96742
(Patent Literature 2) JP-A-2017-112847
(Patent Literature 3) JP-A-2011-36146
(Patent Literature 4) JP-A-hei 3-240487

The present invention provides a method for manufacturing a fermentation product by culturing a microorganism, the method comprising steps (A) to (D):

step (A) of culturing the microorganism with a first culture medium;

step (B) of passing a culture solution containing cultured bacterial cells, raw materials for culture, and the fermentation product through an adsorption tower packed with an adsorbent capable of adsorbing the fermentation product to adsorb the fermentation product from the culture solution to the adsorbent, and then collecting an effluent containing the bacterial cells and the raw materials for culture flowing out from the adsorption tower, wherein a relationship among a size (short diameter) d of the bacterial cell, a pore size $D1$ of the adsorbent, and a minimum void size $D2$ between adsorbent particles, $D1<d<D2$ is satisfied;

step (C) of bringing an eluent into contact with the adsorbent to elute the fermentation product; and step (D) of culturing the microorganism with a second culture medium using the collected effluent containing the bacterial cells and the raw materials for culture.

DETAILED DESCRIPTION OF THE INVENTION

The present invention relates to a method for recovering bacterial cells and unused raw materials for culture contaminated in a fermentation culture solution to enable to efficiently utilize these bacterial cells and raw materials for culture in the production of fermentation products.

As a result of intensive investigations, the present inventors found that, unlike the conventional technology of first separating only the bacterial cells from the fermentation culture solution after culturing the microorganisms, passing the fermentation culture solution contaminated with the bacterial cells, the unused raw material for culture and the fermentation product through a certain resin tower filled with an adsorbent to adsorb the fermentation product to the adsorbent, while passing the solution containing the bacterial cells and the unused raw material for culture through the resin tower, the bacterial cells and the unused raw material for culture can be recovered together with the fermentation product, and the bacterial cells and the unused raw material for culture can be separated from the fermentation product, so that the bacterial cells and the unused raw material for culture can be reused for the production of the subsequent fermentation products.

The present invention enables to effectively utilize the bacterial cells and the raw material for culture in the production of fermentation products, and to economically and efficiently produce the fermentation products by the fermentation method.

The present invention encompasses a method for manufacturing a fermentation product by culturing a microorganism, the method comprising step (A) of culturing the microorganism with a first culture medium; step (B) of passing a culture solution containing cultured bacterial cells, raw materials for culture, and the fermentation product through an adsorption tower packed with an adsorbent capable of adsorbing the fermentation product to adsorb the fermentation product from the culture solution to the adsorbent, and then collecting an effluent containing the bacterial cells and the raw materials for culture flowing out from the adsorption tower, wherein a relationship among a size (short diameter) d of the bacterial cell, a pore size $D1$ of the adsorbent, and a minimum void size $D2$ between adsorbent particles, $D1<d<D2$ is satisfied; step (C) of bringing an eluent, into contact with the adsorbent to elute the fermentation product; and step (D) of culturing the microorganism with a second culture medium using the collected effluent containing the bacterial cells and the raw materials for culture.

In the present invention, the fermentation product may be any material which can be produced outside the cell body by culturing a microorganism.

Preferred examples of the fermentation product includes proteins or polypeptides, such as industrially useful enzymes or biologically active peptides, used in the field of foods, pharmaceuticals, cosmetics, detergents, fibers, medical examinations, or the like.

Examples of the enzyme include oxidoreductases, transferases, hydrolytic enzymes (hydrolases), lyases, isomerases, and synthases (ligases/synthetases).

Among these, hydrolytic enzymes are preferable, cellulase, α-amylase, and protease are more preferable, and cellulase and protease are even more preferable.

The cellulase and protease are preferably alkaline cellulase and alkaline protease.

The alkaline cellulase and the alkaline protease are cellulases and proteases having an optimal pH in the alkaline region.

The cellulase is preferably a cellulase belonging to family 5 in the class of polysaccharide hydrolases (Biochem. J., 280, 309 (1991)), more preferably a cellulase derived from microorganisms, and even more preferably a cellulase derived from *Bacillus* bacteria.

The α-amylase is preferably an α-amylase derived from a microorganism, and more preferably a liquefied amylase derived from *Bacillus* bacterium.

The protease is preferably a protease derived from a microorganism, more preferably a protease derived from bacterium of the genus *Bacillus*, and more preferably a serine protease or a metalloprotease whose active center is a serine residue.

[Step (A)]

The step (A) is a step of culturing a microorganism in a first culture medium.

The microorganism is a microorganism having an ability of producing a fermentation product.

Examples of the microorganism having an ability of producing the proteins or polypeptides include microorganisms belonging to the genus *Staphylococcus, Enterococcus, Listeria, Bacillus,* or *Corynebacterium*. In particular, *Bacillus* bacteria are preferred, and *Bacillus subtilis* is more preferred.

Examples of the *Bacillus* bacterium as an α-amylase-producing microorganism include *Bacillus* sp. strain KSM-K-38 (FERM BP-6946).

Examples of the *Bacillus* bacterium as an alkaline cellulase-producing microorganism include *Bacillus* sp. strain KSM-S237 (FERM BP-7875) and *Bacillus* sp. strain KSM-64 (FERM BP-2886).

Examples of the *Bacillus* bacterium as an alkaline protease-producing microorganism include *Bacillus* sp. strain KSM-64 (FERM P-10482), *Bacillus clausii* strain KSM K-16 (FERM BP-3376), *Bacillus* sp. strain KSM-KP43 (FERM BP-6532), *Bacillus* sp. strain KSM-KP9860 (FERM BP-6534), *Bacillus* No. D-6 (FERM P-1592) (protease E-1), *Bacillus* sp. Y (FERM BP-1029), *Bacillus* SD521 (FERM P-11162), and *Bacillus* sp. strain KSM-9865 (FERM P-18566), strain NCIB12289, and strain NCIB12513.

The microorganism may be a wild-type strain or a mutant strain in which variation, such as insertion, substitution, and deletion, is caused in a nucleotide sequence by a variety of genetic engineering techniques or may be a strain provided with an ability of producing a desired fermentation product by known artificial modification.

As the first culture medium to be used for culturing a microorganism, it is possible to appropriately use a synthetic culture medium, a natural culture medium, or a semi-synthetic culture medium prepared by adding a natural component to a synthetic culture medium each containing a carbon source, a nitrogen source, inorganic salts, and other necessary organic trace nutrient sources that can be assimilated as the raw materials for culture by the microorganism.

Examples of the carbon source include saccharides. Examples of the saccharides include monosaccharides such as glucose, fructose, and xylose; and disaccharides such as sucrose, lactose, and maltose. The saccharide may be an anhydride or a hydrate. Alternatively, a sugar solution containing a saccharide, for example, a sugar solution obtained from starch, molasses (waste molasses), or a sugar solution obtained from cellulose-based biomass, can also be used. In particular, glucose and maltose are preferred from the viewpoint of proliferation of a microorganism.

The concentration of the carbon source in a culture medium is preferably from 5% to 25% (w/v).

Examples of the nitrogen source include extracts, such as yeast extract, meet extract, and fish meat extract; nitrogen-containing compounds, such as ammonia, urea, inorganic and organic ammonium salts, potassium nitrate, and sodium nitrate; corn gluten meal, soy flour, polypeptone, tryptone, peptone, various amino acids, and soybean meal. As these nitrogen sources, commercially available products may be used, or appropriately produced products may be used.

The concentration of the extract in a culture medium is preferably from 0.1% to 2% (w/v) and more preferably from 1 to 2% (w/v) as the dry solid content from the viewpoint of bacterial cell proliferation and productivity.

Examples of the inorganic salt include sulfates, magnesium salts, zinc salts, phosphates, and sodium salts. Examples of the sulfate include magnesium sulfate, zinc sulfate, potassium sulfate, sodium sulfate, and manganese sulfate. Examples of the magnesium salt include magnesium sulfate, magnesium nitrate, and magnesium chloride. Examples of the zinc salt include zinc sulfate, zinc nitrate, and zinc chloride. Examples of the phosphate include sodium hydrogen phosphate, sodium dihydrogen phosphate, trisodium phosphate, dipotassium phosphate, and potassium dihydrogen phosphate. Examples of the sodium salt include sodium sulfate, sodium nitrate, and sodium chloride.

The concentration of the inorganic salt in a culture medium is preferably from 0.5% to 1% (w/v).

The culture medium may appropriately include an antibiotic and trace ingredients as needed.

In the culture of a microorganism, a general method can be used as long as the microorganism can grow and produce a fermentation product of interest.

For example, while the temperature for culturing *Bacillus* bacterium is not particularly limited as long as the proliferation of the microorganism is not badly affected, it is preferably from 20° C. to 48° C. and more preferably from 25° C. to 45° C.

The amount of *Bacillus* bacterium to be inoculated to the culture medium is preferably from 0.1% to 5% (v/v).

The pH (25° C.) of the first culture medium during the culture of *Bacillus* bacterium is preferably from 4 to 10 and more preferably from 5 to 9. The pH of the first culture medium can be adjusted with an appropriate buffer.

The culture period of *Bacillus* bacterium is from 10 hours to 7 days in accordance with the proliferation of the microorganism and is more preferably from 12 hours to 5 days and even more preferably from 24 hours to 4 days. From the viewpoint of improving the carbon source conversion rate described below, the culture period of *Bacillus* bacterium is preferably from 66 hours to 7 days and more preferably from 66 hours to 5 days.

As the culture tank used for the culture, a known tank can be appropriately employed. For example, the culture tank is an aeration agitation culture tank, a bubble tower culture tank, or a fluidized bed culture tank, and any of a batch system, a semi-batch system, and a continuous system may be used.

The aeration agitation culture is preferably performed with a culture medium in which the dissolved oxygen concentration is preferably controlled to be higher than 0 ppm, more preferably 0.5 ppm or more, and further more preferably 1 ppm or more. The stirring rotation speed is preferably a condition that disperses the gas supplied to the culture medium and can be appropriately adjusted in accordance with the scale.

Such culture causes accumulation of a fermentation product in the culture solution. The culture solution contains, in addition to the fermentation product, microorganism cells and unused raw materials for culture. Accordingly, since a procedure for extracting the fermentation product from the culture solution is necessary, in the present invention, the culture solution is subjected to the following step (B).

In the culture solution subjected to the step (B), the concentration of the bacterial cells (OD 600 value) is preferably from 20 to 100, more preferably from 25 to 100, and even more preferably from 30 to 100. This OD 600 value can be measured by the method described in Example below.

In the culture solution subjected to the step (B), the concentration of the fermentation product is preferably from 0.01 to 10 g/L and more preferably from 0.1 to 5 g/L.

In the culture solution subjected to the step (B), the unused raw materials for culture, for example, the residual sugar content, is preferably from 0.1 to 100 g/L, more preferably from 1 to 50 g/L, and more preferably from 5 to 50 g/L.

[Step (B)]

The step (B) of the present invention is a step of passing the culture solution containing cultured bacterial cells, raw materials for culture, and a fermentation product through an adsorption tower packed with an adsorbent capable of adsorbing the fermentation product to adsorb the fermentation product from the culture solution to the adsorbent, and then collecting an effluent containing the bacterial cells and the raw materials for culture flowing out from the adsorption tower, wherein a relationship among the size (short diameter) d of the bacterial cell, the pore size D1 of the adsorbent, and the minimum void size D2 between adsorbent particles, D1<d<D2 is satisfied.

The adsorbent that is used in the present invention is an adsorbent that can absorb and desorb the fermentation product in a culture solution by physical interaction between its pore surface and the fermentation product.

As the adsorbent, for example, a crosslinked polymer synthetic resin can be used. As the adsorbent for adsorbing the proteins or polypeptides, a synthetic resin whose resin matrix is a styrene resin, an acrylic resin, or a methacrylic resin can be used. In particular, from the viewpoint of the adsorption of the fermentation product, a synthetic resin whose resin matrix is a styrene-divinyl benzene copolymer or polymethylmethacrylate is preferred. In addition, it is preferable that the resin matrix does not include a hydrophobic functional group, such as a bromo group, a butyl group, and a phenyl group, in the side chain.

Examples of these resins include styrene-based synthetic adsorbents, such as Amberlite XAD4, Amberlite XAD16HP, Amberlite XAD1180, and Amberlite XAD2000 (these products are available from Organo Corporation), Diaion HP20, Diaion HP20SS, Diaion HP21, Sepabeads SP850, Sepabeads SP825, Sepabeads SP700, and Sepabeads SP70 (these products are available from Mitsubishi Chemical Corporation), and VPOC1062 (available from Bayer AG); methacrylic synthetic adsorbents, such as Diaion HP1MG, Diaion HP2MG, and Sepabeads SP2MGS (these products are available from Mitsubishi Chemical Corporation); and acrylic synthetic adsorbents, such as Amberlite XAD7HP (available from Organo Corporation).

While the form of the adsorbent may be any shape, such as a spherical or uneven shape, a spherical shape is preferred from the viewpoint of separation efficiency.

In the adsorption tower packed with an adsorbent, a relationship among the size (short diameter) d of the bacterial cell, the pore size D1 of the adsorbent, and the minimum void size D2 between adsorbent particles, D1<d<D2 is satisfied. When the size (short diameter) d of the bacterial cell is larger than the pore size D1 of the adsorbent and is smaller than the minimum void size D2 between adsorbent particles, since the bacterial cells in the culture solution that has passed through the adsorption tower flow out together with the raw materials for culture from the adsorption tower, the bacterial cells and the unused raw materials for culture can be collectively collected from the culture solution after culturing of the microorganism and can be separated from the fermentation product.

When microorganism cells are of the same species, the sizes (short diameters) d of the bacterial cells are the same. The size (short diameter) d of the bacterial cell in a culture solution varies depending on the species of the microorganism having an ability of producing a fermentation product but is preferably from 0.1 to 300 μm, more preferably from 0.1 to 10 μm, and even more preferably from 0.3 to 3 μm.

The pore size D1 of the adsorbent is preferably from 1 to 100 nm, more preferably from 5 to 80 nm, and even more preferably from 20 to 60 nm from the viewpoint of the adsorption of the fermentation product. In the specification, the pore size D1 of an adsorbent is an average value.

In addition, the average particle size of the adsorbent is preferably from 30 to 2,000 μm, more preferably from 50 to 1,000 μm, and even more preferably from 70 to 250 μm from the viewpoint of the adsorption of the fermentation product. The average particle size can be measured by dispersing the adsorbent in distilled water and using a particle-size distribution analyzer (for example, LA-920, HORIBA, Ltd.).

Furthermore, a narrower distribution of the particle size of the adsorbent is preferred from the viewpoint of the permeability of bacterial cells. Specifically, the coefficient of variation CV value calculated as the standard deviation σ of the particle size to the average particle size D represented by the following expression (1) is preferably 35% or less, more preferably 25% or less, and even more preferably 10% or less, and the lower limit thereof is preferably 0% or more. From the viewpoint of availability, the lower limit is preferably 1% or more, more preferably 2% or more, and even more preferably 5% or more.

Coefficient of variation $CV$ value (%)=[(standard deviation $\sigma$ of particle size)]/[(average particle size $D$)]×100     Expression (1)

The minimum void size D2 between adsorbent particles is the minimum size of the void between adsorbent particles. The minimum void size D2 between adsorbent particles is preferably from 1 to 500 μm, more preferably from 5 to 300 μm, further more preferably from 7.5 to 200 μm, further more preferably from 10 to 100 μm, and further more preferably from 12 to 50 μm from the viewpoint of the permeability of bacterial cells. The void size between adsorbent particles can be calculated from the average particle size of the adsorbent, and the minimum void size is also an average value.

The ratio of the size (short diameter) d (μm) of the bacterial cell in the culture solution to the pore size D1 (μm) of the adsorbent, [d/D1], is preferably from 1.25 to 2,000, more preferably from 5 to 150, and even more preferably from 10 to 50 from the viewpoint of adsorption of the fermentation product and the viewpoint of the separation efficiency of the bacterial cells and unused raw materials for culture from the fermentation product.

The ratio of the minimum void size D2 (μm) between adsorbent particles to the size (short diameter) d (μm) of the bacterial cell in the culture solution, [D2/d], is preferably from 2 to 2,000, more preferably from 5 to 300, and even more preferably from 10 to 100 from the viewpoint of the permeability of bacterial cells.

The adsorption tower may be packed with the adsorbent such that the size (short diameter) d of the bacterial cell, the pore size D1 of the adsorbent, and the minimum void size D2 between adsorbent particles satisfy the prescribed relationship, and a known method, such as slurry filling, can be used.

Before passing a culture solution through the adsorption tower packed with an adsorbent, it is preferable to wash the adsorbent in advance to remove impurities in the adsorbent.

For example, washing is performed by passing water through the adsorption tower under the conditions for passing of a liquid passing speed (space velocity, SV) of 0.5 to 5/hr and a liquid passing multiple (BV) to the total volume of the adsorbent of 4 to 10. In addition, after passing of an organic solvent aqueous solution, water may be allowed to pass through. The organic solvent aqueous solution to be used for washing is preferably a 10% to 90% (v/v) ethanol aqueous solution.

The conditions for passing of a culture solution may be such that the fermentation product in the culture solution is sufficiently adsorbed to the adsorbent and are, for example, an SV of 0.25 to 10/hr and a BV of 1 to 20. From the viewpoint of the collection efficiency of the fermentation product, more preferred conditions are an SV of 1 to 5/hr and a BV of 2 to 10.

Consequently, since the fermentation product in the culture solution is adsorbed to the adsorbent and the bacterial cells and the raw materials for culture flow out from the adsorption tower, the effluent containing the bacterial cells and the raw materials for culture are collected.

After passing of the culture solution and before step (C), it is preferable to perform a step of washing the adsorbent with a cleaning liquid. As the cleaning liquid for washing the adsorbent, water and an organic solvent aqueous solution can be used. When the proteins or polypeptides are eluted, an organic solvent aqueous solution containing a water-soluble calcium salt described below is preferably used as the cleaning liquid.

[Step (C)]

The step (C) is a step for eluting the fermentation product by bringing an eluent into contact with the adsorbent. The elution step can be performed one or multiple times.

The eluent can desorb and elute the fermentation product adsorbed to the adsorbent. The type and concentration of the eluent are not particularly limited, and examples thereof include alkaline aqueous solutions, salt aqueous solutions, and organic solvent aqueous solutions.

When the proteins or polypeptides are eluted, an organic solvent aqueous solution containing a water-soluble calcium salt as the eluent is preferably used from the viewpoint of collection efficiency and stability.

The water-soluble calcium salt is a calcium salt that is soluble in an aqueous solution, and examples thereof include organic salts, such as calcium lactate, calcium gluconate, and calcium acetate; and inorganic salts, such as calcium nitrate and calcium chloride.

The concentration of the water-soluble calcium salt in an organic solvent aqueous solution is preferably from 0.02 to 30 mM, more preferably from 0.3 to 15 mM, and even more preferably from 1 to 10 mM from the viewpoint of collection efficiency.

Examples of the organic solvent in the organic solvent aqueous solution include polyols and monovalent alcohols having 4 or less carbon atoms. In particular, polyols are preferred from the viewpoint of collection efficiency and stability.

Polyol is a general term for alcohols in which two or more hydrogen atoms of a hydrocarbon are substituted with hydroxy groups, and examples thereof include alkylene glycols, such as ethylene glycol, propylene glycol, 1,3-propanediol, and 1,3-butanediol; polyalkylene glycols, such as diethylene glycol, dipropylene glycol, polyethylene glycol, and polypropylene glycol; and glycerols, such as glycerol, diglycerol, and triglycerol. The weight-average molecular weight of the polyethylene glycol is preferably from 200 to 20,000.

In particular, the polyol has an SP value within a range of from 7 to 20 $(cal/cm^3)^{1/2}$, preferably within a range of from 9 to 18 $(cal/cm^3)^{1/2}$.

Such polyols are preferably propylene glycol (12.6), polyethylene glycol 400 (9.4), and glycerol (16.5) and more preferably propylene glycol (12.6) and polyethylene glycol 400 (9.4) (the values in parentheses indicate the SP values).

The concentration of the organic solvent in an organic solvent aqueous solution is preferably from 20% to 80% (v/v) and even more preferably from 40% to 80% (v/v) from the viewpoint of collection efficiency and stability. When the elution step is performed multiple times, it is preferable to sequentially increase the concentration of the organic solvent in the organic solvent aqueous solution used in each elution step. For example, in a preferred procedure, the elution step of the first stage is performed using a 20% to 60% (v/v) organic solvent aqueous solution, and the elution step of the second stage is performed using a 40% to 80% (v/v) organic solvent aqueous solution.

The conditions for passing the eluent are preferably an SV of from 0.25 to 10/hr and a BV of from 1 to 10 and more preferably an SV of from 1 to 5/hr and a BV of from 2 to 8 from the viewpoint of collection efficiency and liquid volume.

[Step (D)]

The step (D) is a step for culturing the microorganism with a second culture medium using the collected effluent containing the bacterial cells and raw materials for culture. In this step, the collected effluent containing the bacterial cells and raw materials for culture may be partially or wholly used. In addition, when the whole of the effluent is used, from the viewpoint of feeding the second culture medium to a second culture tank, the effluent is preferably concentrated, and the concentration ratio is preferably from 2 to 6 times and more preferably from 3 to 5 times. The collected effluent containing the bacterial cells and raw materials for culture is preferably used in such a manner that the concentration in the second culture medium is preferably 6 mass % or more, more preferably 10 mass % or more, further more preferably 30 mass % or more, and even more preferably 50 mass % or more from the viewpoint of improving the conversion rate of a substrate to a fermentation product.

The volume of the bacterial cells to be subcultured from the first culture medium to the second culture medium is, as percentage based on the liquid volume, preferably 6% (v/v) or more, more preferably 10% (v/v) or more, further more preferably 30% (v/v) or more, and even more preferably 50% (v/v) or more from the viewpoint of improving the conversion rate of the substrate to the fermentation product and the viewpoint of the productivity of the fermentation product.

The volume of the raw materials for culture to be subcultured from the first culture medium to the second culture medium is, as percentage based on the liquid volume, preferably 6% (v/v) or more, more preferably 10% (v/v) or more, further more preferably 30% (v/v) or more, and even more preferably 50% (v/v) or more from the viewpoint of improving the conversion rate of the substrate to the fermentation product and the viewpoint of the productivity of the fermentation product. The quantitative percentage of the subcultured raw materials for culture can be calculated by the following equation based on the sugar content in the culture medium.

Percentage (%) of subculture of the raw materials for culture from first culture medium to second culture medium=[(sugar content derived from first culture medium at the time of starting second culture)]/[(sugar content in first culture solution at the time of ending first culture)]×100

The second culture medium can contain a carbon source and also a nitrogen source, inorganic salts, and other necessary nutrient sources as in the first culture medium. Specifically, the second culture medium is as described above.

Culture of the microorganism in the step (D) may be performed under culture conditions that are the same as or different from those in the culture of the microorganism in the step (A).

The cultured bacterial cells and the unused raw materials for culture can be reused again in production of the fermentation product. That is, after the step (D), a step of repeating the culture of the microorganism once or more, twice or more, or three times or more may be performed by subjecting the culture solution containing the bacterial cells, raw materials for culture, and fermentation product to the step (B) again and using the collected effluent containing the bacterial cells and raw materials for culture.

When the step of culturing the microorganism with a culture medium using the collected effluent containing the bacterial cells and raw materials for culture is repeated twice or more, it is preferable to adjust the pH of the culture medium prior to the culture of the microorganism and/or during the culture of the microorganism with the culture medium using the effluent. While the pH of the culture medium tends to increase or decrease due to accumulation of the medium components by repeating the culture while reusing the bacterial cells and the raw materials for culture, the fermentation product productivity of the microorganism having an ability of producing the fermentation product can be improved by adjusting the pH of the culture medium using the effluent.

The pH of the culture medium using the collected effluent containing the bacterial cells and raw materials for culture during the culture of the microorganism is preferably adjusted to a range from a value 1.2 lower than an average pH value during the first culture, i.e., the culture in the step (A) to a value 1.2 higher than the average pH value, that is, within a range of "(average pH value)±1.2" and more preferably within a range of "(average pH value)±0.6". Incidentally, the pH of a culture medium can be adjusted with an appropriate buffer.

According to the present invention, the raw materials for culture is used for production of a fermentation product without waste by reusing the bacterial cells and the unused raw materials for culture for the subsequent production of the fermentation product. In the present invention, the carbon source conversion rate (%) from the fed carbon source to the fermentation product is preferably 0.5% or more and more preferably 0.6% or more. The carbon source conversion rate is a value obtained by dividing the total weight of the carbon source in the fermentation product by the weight of the fed carbon source. The details of a method for calculating the carbon source conversion rate is described in Examples.

The fermentation product obtained by the present invention can be used as it is, or if necessary, can be further purified, crystallized, or granulated by a known method before use.

Regarding the above-described embodiments, the present invention will further disclose the following manufacturing methods.

<1> A method for manufacturing a fermentation product by culturing a microorganism, the method comprising the following steps (A) to (D):
step (A) of culturing a microorganism with a first culture medium for 10 hours to 7 days;
step (B) of passing a culture solution containing cultured bacterial cells, raw materials for culture, and a fermentation product through an adsorption tower packed with an adsorbent capable of adsorbing the fermentation product to adsorb the fermentation product from the culture solution to the adsorbent, and then collecting an effluent containing the bacterial cells and the raw materials for culture flowing out from the adsorption tower, wherein a relationship among the size (short diameter) d of the bacterial cell, the pore size D1 of the adsorbent, and the minimum void size D2 between adsorbent particles, D1<d<D2 is satisfied;
step (C) of bringing an eluent into contact with the adsorbent to elute the fermentation product; and
step (D) of culturing the microorganism with a second culture medium using the collected effluent containing the bacterial cells and the raw materials for culture,
wherein the volume of the raw materials for culture subcultured from the first culture medium to the second culture medium is 30% (v/v) or more.

<2> A method for manufacturing a fermentation product by culturing a microorganism, the method comprising the following steps (A) to (D):
step (A) of culturing a microorganism with a first culture medium;
step (B) of passing a culture solution containing cultured bacterial cells, raw materials for culture, and a fermentation product through an adsorption tower packed with an adsorbent capable of adsorbing the fermentation product to adsorb the fermentation product from the culture solution to the adsorbent, and then collecting an effluent containing the bacterial cells and the raw materials for culture flowing out from the adsorption tower, wherein a relationship among the size (short diameter) d of the bacterial cell, the pore size D1 of the adsorbent, and the minimum void size D2 between adsorbent particles, D1<d<D2 is satisfied;
step (C) of bringing an eluent into contact with the adsorbent to elute the fermentation product; and
step (D) of culturing the microorganism with a second culture medium using the collected effluent containing the bacterial cells and the raw materials for culture,
wherein the average particle size D of the adsorbent in the step (B) is from 30 to 2,000 μm, and the coefficient of variation CV of particle size represented by the following expression (1) is from 1% to 35%, Coefficient of variation $CV$ value (%)=[(standard deviation $\sigma$ of particle size)]/[(average particle size $D$)]×100    Expression (1).

<3> A method for manufacturing a fermentation product by culturing a microorganism, the method comprising the following steps (A) to (D):
step (A) of culturing a microorganism with a first culture medium;

step (B) of passing a culture solution containing cultured bacterial cells, raw materials for culture, and a fermentation product through an adsorption tower packed with an adsorbent capable of adsorbing the fermentation product to adsorb the fermentation product from the culture solution to the adsorbent, and then collecting an effluent containing the bacterial cells and the raw materials for culture flowing out from the adsorption tower, wherein a relationship among the size (short diameter) d of the bacterial cell, the pore size D1 of the adsorbent, and the minimum void size D2 between adsorbent particles, D1<d<D2 is satisfied;

step (C) of bringing an eluent into contact with the adsorbent to elute the fermentation product; and step (D) of culturing the microorganism with a second culture medium using the collected effluent containing the bacterial cells and the raw materials for culture, wherein the minimum void size D2 in the step (B) is from 1 to 500 µm, and the coefficient of variation CV of particle size represented by the following expression (1) is from 1% to 35%, Coefficient of variation $CV$ value (%)=[(standard deviation σ of particle size)]/[(average particle size $D$)]×100    Expression (1).

EXAMPLES

[Method for Measuring Bacterial Cell Concentration]

A part of a culture solution was fractionated and mixed and diluted 100-fold with a 5% (w/v) sodium chloride aqueous solution, the turbidity at a wavelength of 600 nm was then measured using Hitachi spectrophotometer model U-2000 (Hitachi, Ltd.), and the OD 600 value was calculated from the dilution ratio.

[Method for Measuring Production Amount of Alkaline Protease]

The amount of protein in a culture supernatant obtained by removing the bacterial cells from a culture solution was measured using Protein Assay Rapid Kit wako (manufactured by FUJIFILM Wako Pure Chemical Corporation) to determine the amount of alkaline protease produced and secreted to the outside of cells. The absorbance was measured with a spectrophotometer UV-2450 (manufactured by Shimadzu Corporation).

[Method for Measuring Amount of Maltose Monohydrate]

The amount of maltose monohydrate in a culture supernatant obtained by removing the bacterial cells from a culture solution was measured using F-kit Maltose/Sucrose/D-Glucose (manufactured by Roche Diagnostics GmbH). The absorbance was measured with an absorption spectrophotometer (Benchmark Plus Microplate Reader, manufactured by Bio-Rad Laboratories, Inc.). The amount of maltose monohydrate at the time of ending the culture was defined as the residual sugar content (g/L).

[Calculation of Carbon Source Conversion Rate]

The carbon source conversion rate was calculated by the following expression:

Carbon source conversion rate (%)=[(total weight (g) of carbon source for alkaline protease)]/[(weight (g) of fed maltose monohydrate)]×100.

[Calculation of Recovery Rate of Alkaline Protease]

The alkaline protease recovery rate was calculated based on the protein amounts in a culture solution and a purified enzyme solution by the following expression:

Alkaline protease recovery rate (%)={(protein concentration of purified enzyme solution)×(recovery amount of purified enzyme solution)}/{(protein concentration of culture solution)×(amount of passed culture solution)}×100.

[Method for Measuring pH]

The pH was continuously measured using a pH meter F-635 (manufactured by Broadley James Corporation).

Example 1

(1) Construction of *Bacillus subtilis* Mutant Strain (168_Protease Strain) Including Mutation Induced in Protease Gene Expression Mutation in protease gene expression was introduced. A fragment (A) including a Shine-Dalgarno (SD) sequence (Shine, J. and Dalgarno, L., Proc. Natl. Acad. Sci. USA, 1974, 71: 1342-1346) in an upstream region of a chloramphenicol resistance gene from a trpB gene was amplified by PCR using genomic DNA of *Bacillus subtilis* mutant strain RIK1140 (trpB'A'::PrrnOcatpt1 erm hisC101) (Japanese Patent No. 5847458) as a template and primers trpB-F and PrrnO-catsd-R shown in Table 1. A fragment (B) including an erythromycin resistance gene and a hisC gene was amplified by PCR using primers PrrnO-cat-erm-F and hisC-R2 shown in Table 1.

Subsequently, with reference to the descriptions in JP-A-2002-218989, JP-A-2002-306176, JP-A-2004-122, JP-A-2004-305176, and JP-A-2006-129865, a KP43 protease mutant was produced by sequentially introducing the following mutations (1) to (11) into protease KP43 (alkaline protease including the amino acid sequence of SEQ ID NO: 1, see JP-A-2002-218989).

(1) Replace tyrosine at position 195 with arginine (see JP-A-2002-218989)

(2) Replace aspartic acid at position 369 with asparagine (see JP-A-2002-306176)

(3) Replace threonine at position 65 with proline (see JP-A-2004-122)

(4) Replace valine at position 273 with isoleucine (see JP-A-2004-122)

(5) Replace threonine at position 359 with serine (see JP-A-2004-122)

(6) Replace serine at position 387 with alanine (see JP-A-2004-122)

(7) Replace asparagine at position 166 with glycine (see JP-A-2004-305176)

(8) Replace glycine at position 167 with valine (see JP-A-2004-305176)

(9) Replace alanine at position 133 with serine (see JP-A-2006-129865)

(10) Replace valine at position 134 with threonine (see JP-A-2006-129865)

(11) Insert serine between positions 133 and 134 (see JP-A-2006-129865)

A fragment (C) including a protease gene was amplified by PCR using DNA including a nucleotide sequence of a gene encoding the K943 protease mutant as a template and primers PrrnO-P-F and PrrnO-P-R shown in Table 1.

Subsequently, the resulting fragments and (B) and fragment (C) were linked to each other by a SOE-PCR method using primers trpB-F and hisC-R2 shown in Table 1 to obtain a final PCR product (A+B+C). *Bacillus subtilis* wild-type strain 168 was transformed by a competent method (J. Bacteriol., 1960, 81: 741-746) using the resulting final PCR product to obtain erythromycin resistant and histidine-requiring *Bacillus subtilis* mutant strain 168_protease strain. The hisC101 represents Q318 amber mutation in the hisC gene, and this mutation exhibits a histidine requirement. The hisC101 is linked to trpC2 mutation (tryptophan requiring). Accordingly, *Bacillus subtilis* mutant strain 168_protease strain is a tryptophan-requiring and histidine-requiring strain.

It was verified by PCR using the genome of the resulting *Bacillus subtilis* mutant strain 168_protease strain and subsequent sequencing by a Sanger method that a target mutation was introduced into a predetermined position on the genome.

TABLE 1

| Primer | Sequence (5' → 3') | SEQ ID NO |
|---|---|---|
| trpB-F | gaatgaaataggcagatacggtg attttggcggaaagtttgttcc | 2 |
| Prrn0-catsd-R | ttgatatgcctcctaaattttta tctaaagtgtctcaaagcgact | 3 |
| Prrn0-cat-erm-F | tatgaggatgaagaagcggtgga tgcgtgttcgtgctgacttgca | 4 |
| hisC-R2 | ataaaatgcattttcaaacagga actccttcgcagcggccactcc | 5 |
| Prrn0-P-F | aaaaatttaggaggcatatcaaa tgagaagaaagaaaaaggtctt | 6 |
| Prrn0-P-R | ccaccgcttcttcatcctcatat taattcacaattgccaacgaga | 7 |

(2) First Culturing Step

The transformant obtained above was inoculated in 30 mL of an LB culture medium (10 g/L tryptone, 5 g/L yeast extract, and 5 g/L NaCl) and was cultured in a 500-mL Sakaguchi flask for 20 hours at 30° C. with a shaking speed of 125 r/min to prepare an inoculum (seed culture).

Subsequently, the inoculum was inoculated in 100 mL of a first culture medium (20 g/L tryptone, 10 g/L yeast extract, 10 g/L NaCl, 75 g/L maltose monohydrate, and 7.5 ppm manganese sulfate 4-5 hydrate) at 2% (v/v) and was subjected to aeration agitation culture using a first culture tank at 30° C., 0.5 vvm, and 1200 r/min for 66 hours (first culture). The average pH during the culture was 7.6.

The bacterial cell concentration (OD 600 value) after the culture for 66 hours was 37, and the short diameter of the bacterial cell in the culture solution was about 0.8 µm when observed with an optical microscope. In the culture solution, the residual sugar content was 27 (g/L), and the production amount of alkaline protease was 0.24 (g/L).

(3) Separation Step (Adsorption)

As the adsorption tower, a column (inner diameter: 23 mm, height: 3.6 cm, and volume: 15 mL) was used, and the column was packed with 15 mL of Sepabeads SP2MGS (manufactured by Mitsubishi Chemical Corporation) as an adsorbent by a slurry filling method. The pore size of the adsorbent was 46 nm, the distribution width of the particle size was 120 to 150 µm, and the average particle size was 137.0 µm. The minimum void size between adsorbent particles was 18.6 µm.

Equilibration was performed by passing distilled water through the column at a flow rate of 0.5 mL/min, an SV of 2/hr, and a BV of 5. Subsequently, while performing aeration agitation of the first culture tank, 100 mL of the culture solution from the first culture tank was allowed to pass through the equilibrated column at a flow rate of 0.5 mL/min, an SV of 2/hr, and a BV of 6.7 to adsorb the alkaline protease to the adsorbent, and then the resulting solution containing the bacterial cells and the raw materials for culture and flowing out from the column was collected.

(Washing)

Subsequently, washing was performed by passing 15 mL of a 2 mM calcium chloride aqueous solution as cleaning liquid through the column at a flow rate of 0.5 mL/min, an SV of 2/hr, and a BV of 1.

(Desorption)

The alkaline protease was desorbed by sequentially passing 45 mL of a 40% (v/v) propylene glycol (PG) aqueous solution containing 2 mM calcium chloride and 45 mL of a 80% (v/v) propylene glycol aqueous solution containing 2 mM calcium chloride as eluents through the washed column respectively at a flow rate of 0.5 mL/min, an SV of 2/hr, and a BV of 3 to collect a purified enzyme solution. The recovery rate of the purified alkaline protease was 90.7%.

(4) Second Culture Step

Thirty-five milliliters of a second culture medium having the same composition as that of the first culture medium except that the medium was concentrated 2.86 times was fed in a second culture tank and was subjected to aeration agitation in the second culture tank under the same conditions as above, and 65 ml of the effluent containing the bacterial cells and the raw materials for culture flowing out from the column was added to the tank. The percentages of subculture from the first culture medium to the second culture medium were 65% (v/v) for the bacterial cells, 65% (v/v) for the raw materials (substrate) for culture, and 0% (v/v) for the culture product (alkaline protease).

The pH of the second culture medium was adjusted to 7.0 with 6N sulfuric acid, and aeration agitation culture was then performed at 30° C., 0.5 vvm, and 1200 r/min for 76 hours (second culture). The pH during the culture was within a range of from 7.0 to 7.9, and the average pH was 7.7.

The bacterial cell concentration (OD 600 value) after the culture for 76 hours was 70. The production amount of alkaline protease was 0.51 (g/L).

The carbon source conversion rate of the alkaline protease with respect to the total amount of fed sugar in both the first culture and the second culture was 0.67%.

Example 2

The same procedure as in Example 1 was performed except that the first culture was performed for 97 hours. In the first culture, the bacterial cell concentration (OD 600 value) after the culture for 97 hours was 30, and in the culture solution, the residual sugar content was 13 (g/L), and the production amount of alkaline protease was 0.27 (g/L). In the second culture, the bacterial cell concentration (OD 600 value) after the culture for 76 hours was 73, and the production amount of alkaline protease was 0.53 (g/L).

In addition, the carbon source conversion rate of the alkaline protease with respect to the total amount of fed sugar in both the first culture and the second culture was 0.71%.

Example 3

The same procedure as in Example 1 was performed except that the first culture was performed for 122 hours. In the first culture, the bacterial cell concentration (OD 600 value) after the culture for 122 hours was 29, and in the culture solution, the residual sugar content was 10 (g/L), and the production amount of alkaline protease was 0.27 (g/L). In the second culture, the bacterial cell concentration (OD 600 value) after the culture for 76 hours was 68, and the production amount of alkaline protease was 0.59 (g/L).

In addition, the carbon source conversion rate of the alkaline protease with respect to the total amount of fed sugar in both the first culture and the second culture was 0.77%.

Example 4

The same procedure as in Example 1 was performed except that the first culture was performed for 144 hours. In the first culture, the bacterial cell concentration (OD 600 value) after the culture for 144 hours was 26, and in the culture solution, the residual sugar content was 0 (g/L), and the production amount of alkaline protease was 0.28 (g/L). In the second culture, the bacterial cell concentration (OD 600 value) after the culture for 76 hours was 60, and the production amount of alkaline protease was 0.40 (g/L).

In addition, the carbon source conversion rate of the alkaline protease with respect to the total amount of fed sugar in both the first culture and the second culture was 0.61%.

Example 5

The same procedure as in Example 1 was performed except that the first culture was performed for 7 days, i.e. 168 hours. In the first culture, the bacterial cell concentration (OD 600 value) after the culture for 168 hours was 22, and in the culture solution, the residual sugar content was 0 (g/L), and the production amount of alkaline protease was 0.27 (g/L). In the second culture, the bacterial cell concentration (OD 600 value) after the culture for 76 hours was 58, and the production amount of alkaline protease was 0.36 (g/L).

In addition, the carbon source conversion rate of the alkaline protease with respect to the total amount of fed sugar in both the first culture and the second culture was 0.56%.

Comparative Example 1

Regarding the first culture in Example 1, the culture was performed until the residual sugar content in the culture solution reached 0 (g/L), and the step after the separation step was not performed.

The bacterial cell concentration (OD 600 value) after the culture for 65 hours was 37.

The carbon source conversion rate of the alkaline protease with respect to the amount of fed sugar in the first culture was 0.48%.

Comparative Example 2

The same procedure as in Example 1 was performed except that after the first culture, the bacterial cells were collected by aseptic centrifugation (5° C., 9,000 r/min, 10 min) of the culture solution, without using a column, and were subcultured to a second culture medium. The pH during the culture was within a range of from 6.5 to 8.1, and the average pH was 7.6.

The percentages of subculture from the first culture medium to the second culture medium were 100% (v/v) for the bacterial cells, 0% (v/v) for the raw materials (substrate) for culture, and 0% (v/v) for the culture product (alkaline protease).

The bacterial cell concentration (OD 600 value) after the culture for 76 hours was 44. In addition, the production amount of alkaline protease was 0.29 (g/L).

The carbon source conversion rate of the alkaline protease with respect to the total amount of fed sugar in both the first culture and the second culture was 0.47%.

The conditions and carbon source conversion rates in Examples 1 to 5 and Comparative Examples 1 and 2 are shown in Table 2.

TABLE 2

| | | | Example 1 | Example 2 | Example 3 | Example 4 | Example 5 | Comparative Example 1 | Comparative Example 2 |
|---|---|---|---|---|---|---|---|---|---|
| Step (A) | First culture medium | | | | | | | | |
| | Amount of fed sugar | [g/L] | 75 | 75 | 75 | 75 | 75 | 75 | 75 |
| | Average pH | [—] | 7.6 | 7.5 | 7.6 | 7.6 | 7.8 | 7.6 | 7.6 |
| | Bacterial cell concentration (OD 600 value) | [Abs.] | 37 | 30 | 29 | 26 | 22 | 37 | 37 |
| | Residual sugar content | [g/L] | 27 | 13 | 10 | 0 | 0 | 0 | 27 |
| | Production amount of alkaline protease | [g/L] | 0.24 | 0.27 | 0.27 | 0.28 | 0.27 | 0.27 | 0.24 |
| Step (B) | Type of adsorbent | | SP2MGS | SP2MGS | SP2MGS | SP2MGS | SP2MGS | — | (Centrifugation) |
| Step (C) | Eluent | | PG | PG | PG | PG | PG | — | — |
| Step (D) | Second culture medium | | | | | | | | |
| | Subculture percentage — Bacterial cells | [%] | 65 | 65 | 65 | 65 | 65 | — | 100 |
| | Subculture percentage — Raw materials for culture | [%] | 65 | 65 | 65 | 65 | 65 | — | 0 |
| | Subculture percentage — Alkaline protease | [%] | 0 | 0 | 0 | 0 | 0 | — | 0 |
| | Amount of fed sugar | [g/L] | 75 | 75 | 75 | 75 | 75 | — | 75 |
| | pH range | [—] | 7.0~7.9 | 7.3~7.8 | 7.3~7.8 | 7.2~7.9 | 7.0~7.9 | — | 6.5~8.1 |
| | Average pH | [—] | 7.7 | 7.6 | 7.5 | 7.7 | 7.7 | — | 7.6 |
| | Bacterial cell concentration (OD 600 value) | [Abs.] | 70 | 73 | 68 | 60 | 58 | — | 44 |
| | Production amount of alkaline protease | [g/L] | 0.51 | 0.53 | 0.59 | 0.40 | 0.36 | — | 0.29 |
| Carbon source conversion rate | | [%] | 0.67 | 0.71 | 0.77 | 0.61 | 0.56 | 0.48 | 0.47 |

Example 6

As in Example 1, the first culture step, the separation step, and the second culture step were performed. The percentages of subculture from the first culture medium to the second culture medium were 65% (v/v) for the bacterial cells, 65% (v/v) for the raw materials (substrate) for culture, and 0% (v/v) for the culture product (alkaline protease). In addition, the bacterial cell concentration (OD 600 value) after the completion of the second culture step was 70, and in the culture solution, the residual sugar content was 27 (g/L), and the production amount of alkaline protease was 0.51 (g/L). The pH during the second culture was within a range of from 7.0 to 7.9, and the average pH was 7.7.

The carbon source conversion rate of the alkaline protease with respect to the total amount of fed sugar in both the first culture and the second culture was 0.67%.

After the completion of the second culture step, the same procedure as the separation step in Example 1 was performed to collect the effluent containing the bacterial cells and the raw materials for culture, and 65 mL of the effluent was then added to a third culture tank containing 35 mL of a third culture medium having the same composition as that of the second culture medium. The percentages of subculture from the second culture medium to the third culture medium were 65% (v/v) for the bacterial cells, 65% (v/v) for the raw materials (substrate) for culture, and 0% (v/v) for the culture product (alkaline protease).

The pH of the third culture medium was adjusted to 7.0 with 6N sulfuric acid, and aeration agitation culture was then performed at 30° C., 0.5 vvm, and 1200 r/min for 52 hours (third culture). The pH during the culture was within a range of 7.0 to 7.9, and the average pH was 7.7.

The bacterial cell concentration (OD 600 value) after the culture for 52 hours was 85. In addition, the production amount of alkaline protease was 0.44 (g/L).

The carbon source conversion rate of the alkaline protease with respect to the total amount of fed sugar in all the first culture, the second culture, and the third culture was 0.71%.

Example 7

The same procedure as in Example 6 was performed except that the pH of the second culture medium and the third culture medium was not adjusted at the time of starting the culture. The pH during the second culture was within a range of from 7.3 to 8.4, and the average pH was 7.9. In addition, the pH during the third culture was within a range of from 7.7 to 8.9, and the average pH was 8.3.

The percentages of subculture from the first culture medium to the second culture medium were 65% (v/v) for the bacterial cells, 65% (v/v) for the raw materials (substrate) for culture, and 0% (v/v) for the culture product (alkaline protease). In addition, the bacterial cell concentration (OD 600 value) after the completion of the second culture step was 72, and in the culture solution, the residual sugar content was 27 (g/L), and the production amount of alkaline protease was 0.47 (g/L).

The carbon source conversion rate of the alkaline protease with respect to the total amount of fed sugar in both the first culture and the second culture was 0.63%.

The percentages of subculture from the second culture medium to the third culture medium were 65% (v/v) for the bacterial cells, 65% (v/v) for the raw materials (substrate) for culture, and 0% (v/v) for the culture product (alkaline protease).

The bacterial cell concentration (OD 600 value) after the third culture for 52 hours was 83. In addition, the production amount of alkaline protease was 0.31 (g/L).

The carbon source conversion rate of the alkaline protease with respect to the total amount of fed sugar in all the first culture, the second culture, and the third culture was 0.61%.

The conditions and carbon source conversion rates in Examples 6 and 7 are shown in Table 3.

TABLE 3

|  |  |  |  | Example 6 | Example 7 |
|---|---|---|---|---|---|
| Step (A) | First culture medium | | | | |
| | Amount of fed sugar | [g/L] | | 75 | 75 |
| | Average pH | [-] | | 7.6 | 7.6 |
| | Bacterial cell concentration (OD 600 value) | [Abs.] | | 37 | 37 |
| | Residual sugar content | [g/L] | | 27 | 27 |
| | Production amount of alkaline protease | [g/L] | | 0.24 | 0.24 |
| Step (B1) | Type of adsorbent | | | SP2MGS | SP2MGS |
| Step (C1) | Eluent | | | PG | PG |
| Step (D1) | Second culture medium | | | | |
| | Subculture percentage | Bacterial cells | [%] | 65 | 65 |
| | | Raw materials for culture | [%] | 65 | 65 |
| | | Alkaline protease | [%] | 0 | 0 |
| | Amount of fed sugar | [g/L] | | 75 | 75 |
| | pH range | [-] | | 7.0~7.9 | 7.3~8.4 |
| | Average pH | [-] | | 7.7 | 7.9 |
| | Bacterial cell concentration (OD 600 value) | [Abs.] | | 70 | 72 |
| | Residual sugar content | [g/L] | | 27 | 77 |
| | Production amount of alkaline protease | [g/L] | | 0.51 | 0.47 |
| Step (B2) | Type of adsorbent | | | SP2MGS | SP2MGS |
| Step (C2) | Eluent | | | PG | PG |
| Step (D2) | Third culture medium | | | | |
| | Subculture percentage | Bacterial cells | [%] | 65 | 65 |
| | | Raw materials for culture | [%] | 65 | 65 |
| | | Alkaline protease | [%] | 0 | 0 |
| | Amount of fed sugar | [g/L] | | 75 | 75 |
| | pH range | [-] | | 7.0~7.9 | 7.7~8.9 |
| | Average pH | [-] | | 7.7 | 8.3 |
| | Bacterial cell concentration (OD 600 value) | [Abs.] | | 85 | 83 |
| | Production amount of alkaline protease | [g/L] | | 0.44 | 0.31 |
| | Carbon source conversion rate | [%] | | 0.71 | 0.61 |

It was confirmed from Table 2 that according to the method of the present invention, bacterial cells and raw materials for culture can be used without waste and that the conversion rate of maltose monohydrate as the carbon source in the culture medium to alkaline protease is high. It was also confirmed from Table 3 that when a step of culturing a microorganism with a culture medium using a collected effluent is repeated twice or more, it is preferable to adjust the pH of the culture medium for improving the productivity of the fermentation product.

The invention claimed is:

1. A method for manufacturing a fermentation product by culturing a microorganism, the method comprising steps (A) to (D):
   step (A) of culturing the microorganism in a first culture medium;
   step (B) of passing a culture solution containing cultured bacterial cells, raw materials for culture, and the fermentation product through an adsorption tower packed with an adsorbent capable of adsorbing the fermentation product to adsorb the fermentation product from the culture solution to the adsorbent, and then collecting an effluent containing the bacterial cells and the raw materials for culture flowing out from the adsorption tower, wherein a relationship among a size (short diameter) d of the bacterial cell, a pore size D1 of the adsorbent, and a minimum void size D2 between adsorbent particles, D1<d<D2 is satisfied, and the coefficient of variation CV value of particle size of the adsorbent represented by the following Expression (1) is from 1% to 35%, Coefficient of variation $CV$ value (%)=[(standard deviation $\sigma$ of particle size)]/[(average particle size $D$)]×100  Expression (1);

step (C) of bringing an eluent into contact with the adsorbent to elute the fermentation product; and
   step (D) of culturing the microorganism with a second culture medium using the collected effluent containing the bacterial cells and the raw materials for culture.

2. The method for manufacturing a fermentation product according to claim 1, the method further comprising a step of repeating the procedure of the steps (B) to (D) once or more after the step (D).

3. The method for manufacturing a fermentation product according to claim 2, wherein in the step (D), the pH of the culture medium using the collected effluent containing the bacterial cells and the raw materials for culture is adjusted to a range from a value 1.2 lower than an average pH value during the culture in the step (A) to a value 1.2 higher than the average pH value.

4. The method for manufacturing a fermentation product according to claim 1, wherein the microorganism is a *Bacillus* bacterium.

5. The method for manufacturing a fermentation product according to claim 1, wherein the fermentation product is a hydrolase.

6. The method for manufacturing a fermentation product according to claim 5, wherein the hydrolase is alkali cellulase or alkaline protease.

7. The method for manufacturing a fermentation product according to claim 1, wherein in the step (A), the microorganism is cultured for from 10 hours to 7 days in the first culture medium.

8. The method for manufacturing a fermentation product according to claim 1, wherein the average particle size D of the adsorbent in the step (B) is from 30 to 2,000 μm.

9. The method for manufacturing a fermentation product according to claim 1, wherein the minimum void size D2 in the step (B) is from 1 to 500 μm.

10. The method for manufacturing a fermentation product according to claim 1, wherein in the step (B), the coefficient of variation CV of particle size represented by the following expression (1) of the adsorbent in the step (B) is from 1% to 35%, Coefficient of variation $CV$ value (%)=[(standard deviation $\sigma$ of particle size)]/[(average particle size $D$)]×100  Expression (1).

11. The method for manufacturing a fermentation product according to claim 1, wherein in the step (B), the ratio of the size (short diameter) d (μm) of the bacterial cell in the culture solution to the pore size D1 (μm) of the adsorbent, [d/D1], is from 1.25 to 2,000.

12. The method for manufacturing a fermentation product according to claim 1, wherein in the step (B), the ratio of the minimum void size D2 (μm) between adsorbent particles to the size (short diameter) d (μm) of the bacterial cell in the culture solution, [D2/d], is from 2 to 2,000.

13. The method for manufacturing a fermentation product according to claim 1, wherein the microorganism in the step (A) is one or more chosen from the microorganisms belonging to genus *Staphylococcus*, *Enterococcus*, *Listeria*, *Bacillus*, or *Corynebacterium*.

14. The method for manufacturing a fermentation product according to claim 1, wherein the microorganism in the step (A) is one or more chosen from the microorganisms belonging to genus *Bacillus*.

15. The method for manufacturing a fermentation product according to claim 1, wherein in the culture solution subjected to the step (B), the concentration of the bacterial cells (OD 600 value) is from 20 to 100.

16. The method for manufacturing a fermentation product according to claim 1, wherein the concentration of the fermentation product in the culture solution of the step (B) is from 0.01 to 10 g/L.

17. The method for manufacturing a fermentation product according to claim 1, wherein the adsorbent in the step (B) is a crosslinked polymer synthetic resin.

18. The method for manufacturing a fermentation product according to claim 1, wherein the pore size D1 of the adsorbent in the step (B) is from 1 to 100 nm.

19. The method for manufacturing a fermentation product according to claim 1, wherein in the step (D) the effluent containing the bacterial cells and raw materials for culture collected in the step (B) is partially or wholly used.

20. The method for manufacturing a fermentation product according to claim 19, wherein in the step (D), when the whole of the effluent is used, the effluent containing the bacterial cells and the raw materials for culture is concentrated to a concentration ratio of from 2 to 6 times.

* * * * *